United States Patent
Eda et al.

(10) Patent No.: US 7,206,622 B2
(45) Date of Patent: Apr. 17, 2007

(54) DEVICE TO MEASURE DEGREE OF ACQUISITION AND METHOD FOR MEASURING DEGREE OF ACQUISITION

(75) Inventors: Hideo Eda, Tokyo (JP); Sayaka Tanaka, Tokyo (JP); Takanori Maesako, Osaka (JP); Katsuo Sugai, Osaka (JP)

(73) Assignee: National Institute of Information and Communications Technology, Tokyo (JP)

( * ) Notice: Subject to any disclaimer, the term of this patent is extended or adjusted under 35 U.S.C. 154(b) by 338 days.

(21) Appl. No.: 10/696,797

(22) Filed: Oct. 30, 2003

(65) Prior Publication Data

US 2004/0210119 A1 Oct. 21, 2004

(30) Foreign Application Priority Data

Nov. 1, 2002 (JP) ............................ P2002-356007

(51) Int. Cl.
*A61B 5/00* (2006.01)

(52) U.S. Cl. ...................... 600/340; 600/300; 600/322; 600/323

(58) Field of Classification Search ................ 600/309, 600/310, 322, 323, 340, 382, 383

See application file for complete search history.

(56) References Cited

FOREIGN PATENT DOCUMENTS

| JP | H09-149894 A | 6/1997 |
|----|--------------|--------|
| JP | 2002-065678 A | 3/2002 |
| JP | 2002-172106 A | 6/2002 |
| JP | 2002-2366096 A | 8/2002 |

OTHER PUBLICATIONS

Hoshi et al., Near-Infrared Optical Detection of Sequential Brain Activation in the Prefrontal Cortex during Mental Tasks (May 1997), NeuroImage, vol. 5, p. 292-297.*
Baird et al., Frontal Lobe Activation during Object Permanence: Data from Near-Infrared Spectroscopy (Aug. 2002), NeuroImage, vol. 16, p. 1120-1126.*
Sakatani et al., Language-Activated Cerebral Blood Oxygenation and Hemodynamic Changes of the Left Prefrontal Cortex in Poststroke Aphasic Patients : A Near-Infrared Spectroscopy Study (Jul. 1998), Stroke, vol. 29, p. 1299-1304.*
Sackler Institute, Preliminary Synthesis of the First High Level Forum on Learning Sciences and Brain ResearchI: Potential Implications for Education Policies and Practices, New York City, NY, Jun. 16-17, 2000 (OECD—CERI Jan. 20, 2001) pp. 1-38.

* cited by examiner

*Primary Examiner*—Eric Winakur
*Assistant Examiner*—Etsub Berhanu

(57) ABSTRACT

A device 4 to measure a degree of acquisition is provided to present objective scientific data of an educational effect by applying brain science to an educational field. A device 4 to measure a degree of acquisition comprises a measuring portion 1 that measures a blood amount or/and a blood component amount in a predetermined measuring region S of brains of a subject P, a diachronic change data producing portion 2 that obtains the blood amount or/and the blood component amount measured in the above-mentioned measuring portion 1 chronologically and produces diachronic change data as data showing diachronic change of the blood amount or/and the blood component amount, and a waveform output portion 3 that outputs a waveform of the diachronic change data in each work in a comparable manner in case the subject P repeatedly conducts the predetermined work several times.

10 Claims, 8 Drawing Sheets

| trial | Drawing range (mm) | Drawing line number | Drawing interval (mm) |
|---|---|---|---|
| 1 | 29 | 19 | 1.53 |
| 2 | 26 | 20 | 1.30 |
| 3 | 25 | 21 | 1.19 |
| 4 | 24 | 21 | 1.14 |
| 5 | 24.5 | 21 | 1.17 |

DEVICE TO MEASURE DEGREE OF ACQUISITION AND METHOD FOR MEASURING DEGREE OF ACQUISITION

BACKGROUND OF THE INVENTION

1. Background of the Invention and Related Art Statement

This invention relates to a device for measuring a degree of acquisition to a target work for a subject by making use of a change of brain activities of the subject.

A variety of methods have been presented to enhance an educative effect and a new educational method is also being developed employing personal computers.

It is essential for any educational mode to grasp intelligibility of a learner and to verify an educational effect in order to establish an achievement or a method of education. If a learner proceeds to a next step without mastering a step or a learner is forced to get education of a step that the learner has already mastered, the learner may feel a disincentive and it is not preferable from a viewpoint of efficiency. Then, intelligibility of a leaner is estimated based on, for example, an educator's subjective judgment or a score of an examination. An example of an educational system with a computer is found in Japan Patent Publication No. 8-227266.

Japan Patent Publication No. 8-227266

As mentioned above, however, the educator's subjective judgment largely depends on an educational ability of each educator, which makes it difficult to establish an objective educational method. Further, a degree of achievement might not be estimated accurately from the score of the examination such as a learner might not be able to demonstrate the learner's true ability in the examination due to an intense pressure, although the score of the examination is apparently superior in objectivity. In addition, there is also a case that education does not make progress as a consequence of defect of interpersonal relationship such as learning disability.

In the mean time, a variety of devices that can measure brain activities without constraining a movement of a subject in a non-invasive manner have been developed apart from an electroencephalograph, a CT scanner or an MRI system and a progress in a study of brain science has been amazing.

The present claimed invention intends to offer an objective scientific data of educational effect by applying the brain science to an educational field. More specifically, the present claimed inventor has found that intelligibility for performing a work is closely related to diachronic change of a blood amount or/and a blood component amount in a predetermined region of brains as a result of repeated experiments and a committed review. The present invention intends to develop a preferable educational method confirmed by scientific data of an educational effect or to provide a simple measure that is effective to set objective guidelines for an educational curriculum by making use of the above-mentioned relationship.

SUMMARY OF THE INVENTION

A device to measure a degree of acquisition in accordance with the present claimed invention comprises a measuring portion that measures a blood amount or/and a blood component amount in a predetermined measuring region of brains of a subject, a diachronic change data producing portion that obtains the blood amount or/and the blood component amount measured in the above-mentioned measuring portion chronologically and produces diachronic change data as data showing diachronic change of the blood amount or/and the blood component amount, and a waveform output portion that outputs a waveform of the diachronic change data in each work in a comparable manner in case the subject repeatedly conducts the predetermined work several times.

In accordance with the arrangement, a degree of acquisition to a work for a subject can be obtained objectively from the waveform of diachronic change data waveform of the blood amount or/and the blood amount component in a predetermined region of brains of the subject. As a result of this, it is possible for an educator to obtain a degree of acquisition of a learner during education without imposing a special burden such as an examination to the learner and it is also possible to provide a development of a new educational method or an establishment of objective guidelines of an educational curriculum with a big potential. In addition, since the device only detects diachronic change of the blood amount or/and the blood amount component and outputs waveforms, there is no need of a complicated processing nor mechanisms such as an image processing.

Further, since the device measures a blood volume amount or/and a blood component amount, it is possible to conduct a measurement under a non-invasive condition without constraining a movement of the subject with a simple arrangement, thereby to conduct a measurement under a natural environment, for example, by making use of a near-infrared spectroscopy. Further, since the near-infrared spectroscopy is superior in time resolution, a degree of acquisition for a learner can be obtained on the spot in real time.

It is also possible to find out a difficulty level of each work for a subject in case the subject conducts a plurality of different works. In this case it is preferable that a device to measure a degree of acquisition comprises a measuring portion that measures a blood amount or/and a blood component amount in a predetermined measuring portion of brains of a subject, a diachronic change data producing portion that obtains the blood amount or/and the blood component amount measured in the above-mentioned measuring portion chronologically and produces diachronic change data as data showing diachronic change of the blood amount or/and the blood component amount, and a waveform output portion that outputs a waveform of the diachronic change data in each work in a comparable manner in case the subject conducts a work and other work different from the former work. In accordance with the arrangement, it is possible for an educator to grasp strong and weak points of the subject previously, which makes it possible to educate the subject appropriately.

More concretely, represented is the device to measure a degree of acquisition wherein the measuring portion measures at least an amount of deoxyhemoglobin in blood and the waveform output portion outputs the waveform of the diachronic change data in accordance with the amount of deoxyhemoglobin. According to a result of repeated experiments and a committed review of the present claimed inventor, it becomes clear that a degree of acquisition is closely related to a diachronic change of an amount of deoxyhemoglobin.

Further, the degree of acquisition can be obtained with a single work if we focus on a diachronic change of an amount of deoxyhemoglobin. In this case, it is preferable that a device to measure a degree of acquisition comprises a measuring portion that measures an amount of deoxyhemoglobin in a predetermined measuring region of brains of a subject, a diachronic change data producing portion that obtains the amount of deoxyhemoglobin measured in the above-mentioned measuring portion chronologically and produces diachronic change data as data showing diachronic change of the amount of deoxyhemoglobin, and a waveform output portion that outputs a waveform of diachronic change data in case the subject conducts a predetermined work.

In order to automatically determine a degree of acquisition, it is preferable that the device further comprises an acquisition degree calculating portion that calculates a degree of acquisition to each work for the subject. More specifically, it is represented that the acquisition degree calculating portion determines that the degree of acquisition to the work for the subject is high in case the amount of deoxyhemoglobin tends to remain generally unchanged or to decrease in the diachronic change data during the work in spite of the lapse of time.

As a preferable measuring region represented is an area corresponding to a higher brain function portion. More concretely, it is preferable that the predetermined measuring region is set at the frontal lobe. This is because the measurement can be done easily and it would be little burden to the subject.

As mentioned above, as a preferable concrete embodiment of the measuring portion represented is that measuring the blood amount or/and the blood component amount by making use of a near-infrared spectroscopy. In this case, the measuring portion is not necessarily be a type of multi-channels, and a type of one channel will do to produce a sufficient effect as the present claimed invention.

In case a posture when the subject conducts a work is different from a posture when the subject does not conduct the work, there might be an error in determining a degree of acquisition because of an offset against the diachronic change data due to brain activities in connection with a change of the posture. In order to avoid this influence, it is preferable that the blood amount or/and the blood component amount is measured in a state the subject does not conduct the work with taking a posture of conducting the work and a diachronic change of a value that is calculated by subtracting a blood amount or/and a blood component amount when the subject conducts the work from the blood amount or/and the blood component amount measured in the above state is assumed to be the diachronic change data.

In short, a method for measuring a degree of acquisition may be so arranged that a blood amount or/and a blood component amount in a predetermined measuring region of brains of a subject is measured chronologically with the use of a near-infrared spectroscopy, diachronic change data as data showing diachronic change of the blood amount or/and the blood component amount is produced and a degree of acquisition to a work for a subject is determined based on the diachronic change data.

DETAILED DESCRIPTION OF THE PREFERRED EMBODIMENTS

An embodiment of the present claimed invention will be described in detail with reference to the accompanying drawings.

Figure 1:
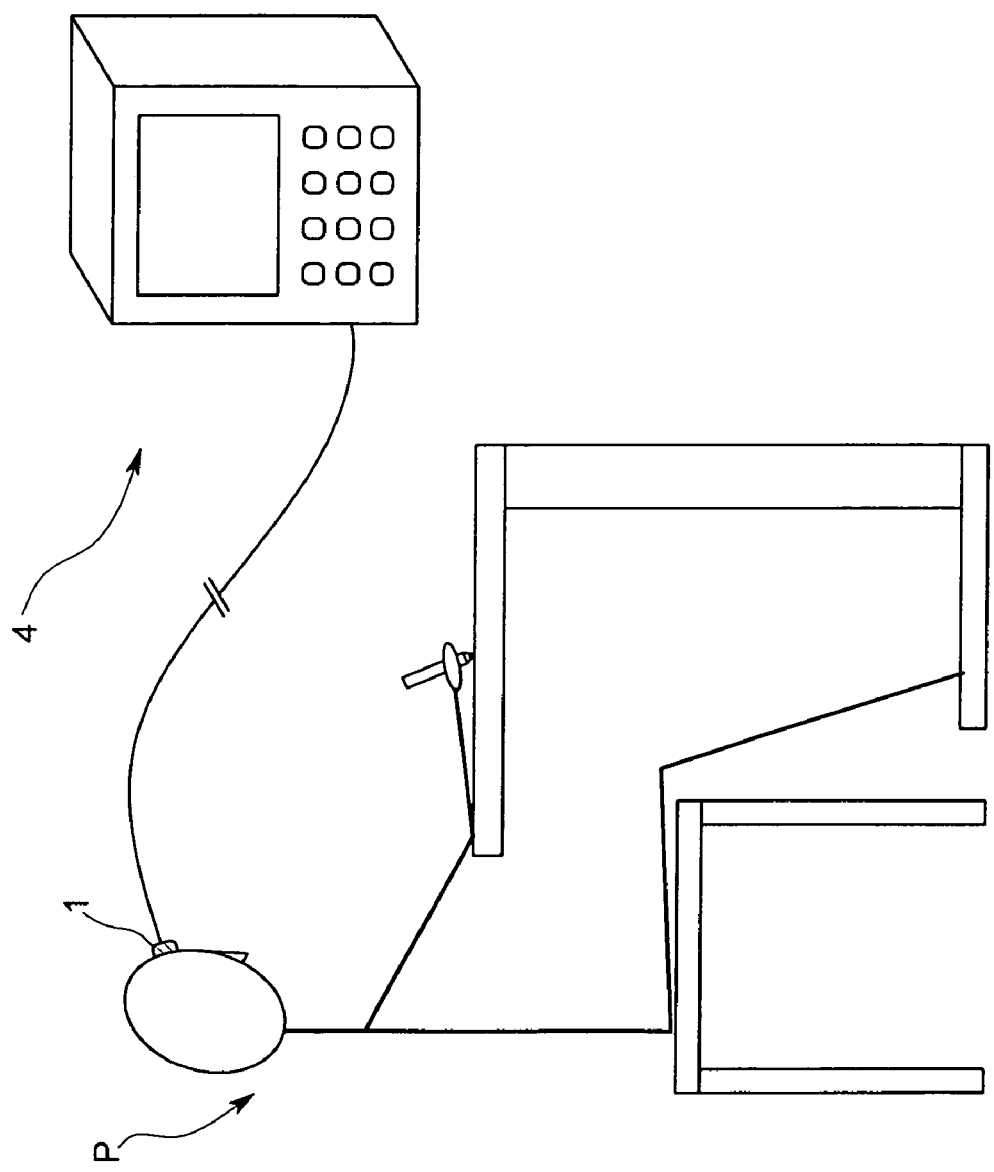
FIG. 1 is a schematic view showing a device to measure a degree of acquisition in accordance with one embodiment of the present claimed invention.
Figure 3:
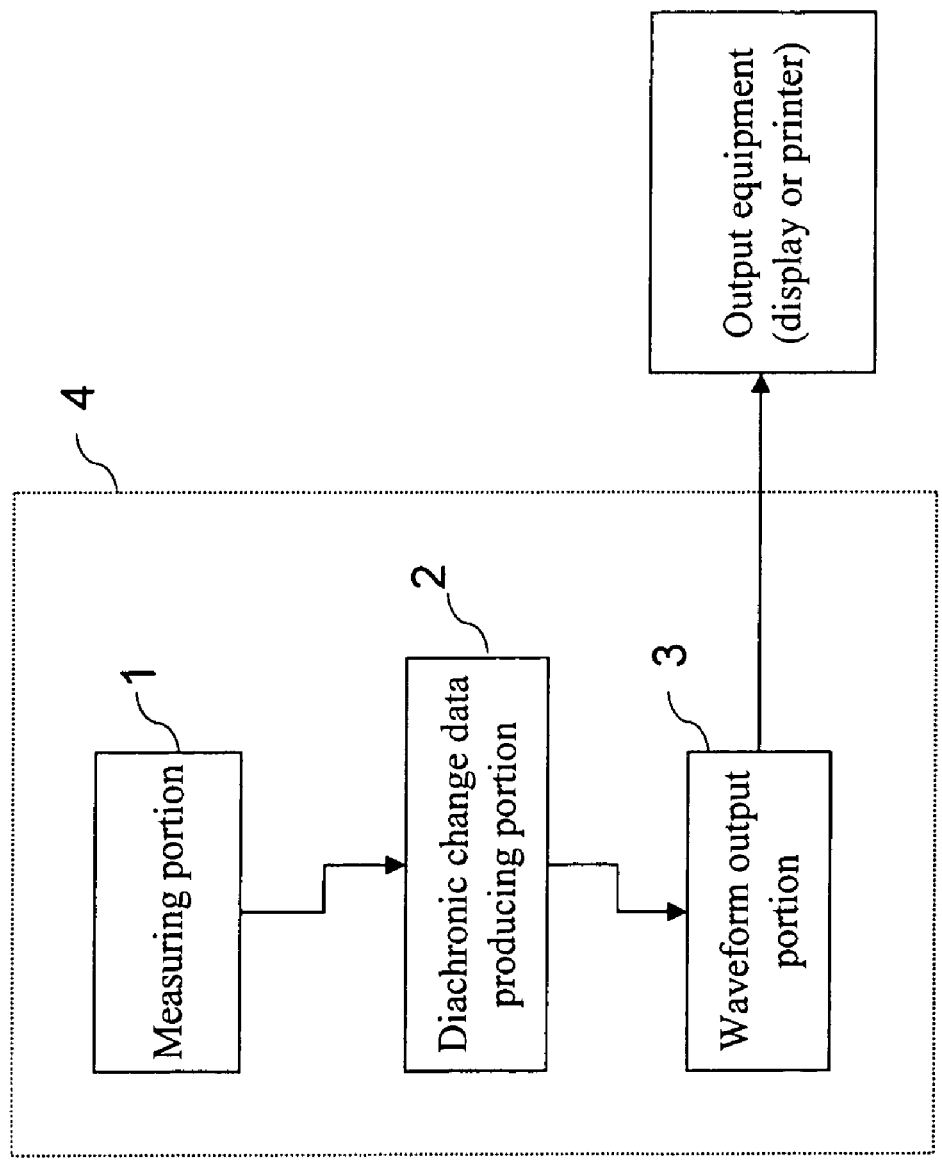
FIG. 3 is a whole functional structural view of the device to measure a degree of acquisition in accordance with the embodiment.

A device 4 to measure a degree of acquisition in accordance with the embodiment comprises, as shown in FIG. 1 and FIG. 3, a measuring portion 1 that measures a blood component amount in a predetermined measuring region S of brains of a subject P, a diachronic change data producing portion 2 that obtains the blood component amount measured in the above-mentioned measuring portion 1 chronologically and produces diachronic change data as data showing diachronic change of the blood component amount and a waveform output portion 3 that outputs a waveform of the diachronic change data in each work in a comparable manner in case the subject P repeatedly conducts a predetermined work several times.

Each portion will be described more concretely. The measuring portion 1 makes use of an NIRS (near-infrared spectroscopy) wherein near-infrared light of a plurality of different wave lengths (three wave lengths in this embodiment) irradiated from a semiconductor laser or the like incidents on the predetermined measuring region and each of the near-infrared light reflecting off inside the brains is received by a photo acceptance element and measures an amount of oxyhemoglobin and deoxyhemoglobin in blood or tissue by a logarithm of proportion of the incident light to the reflected light, more specifically, absorbency.

Figure 2:
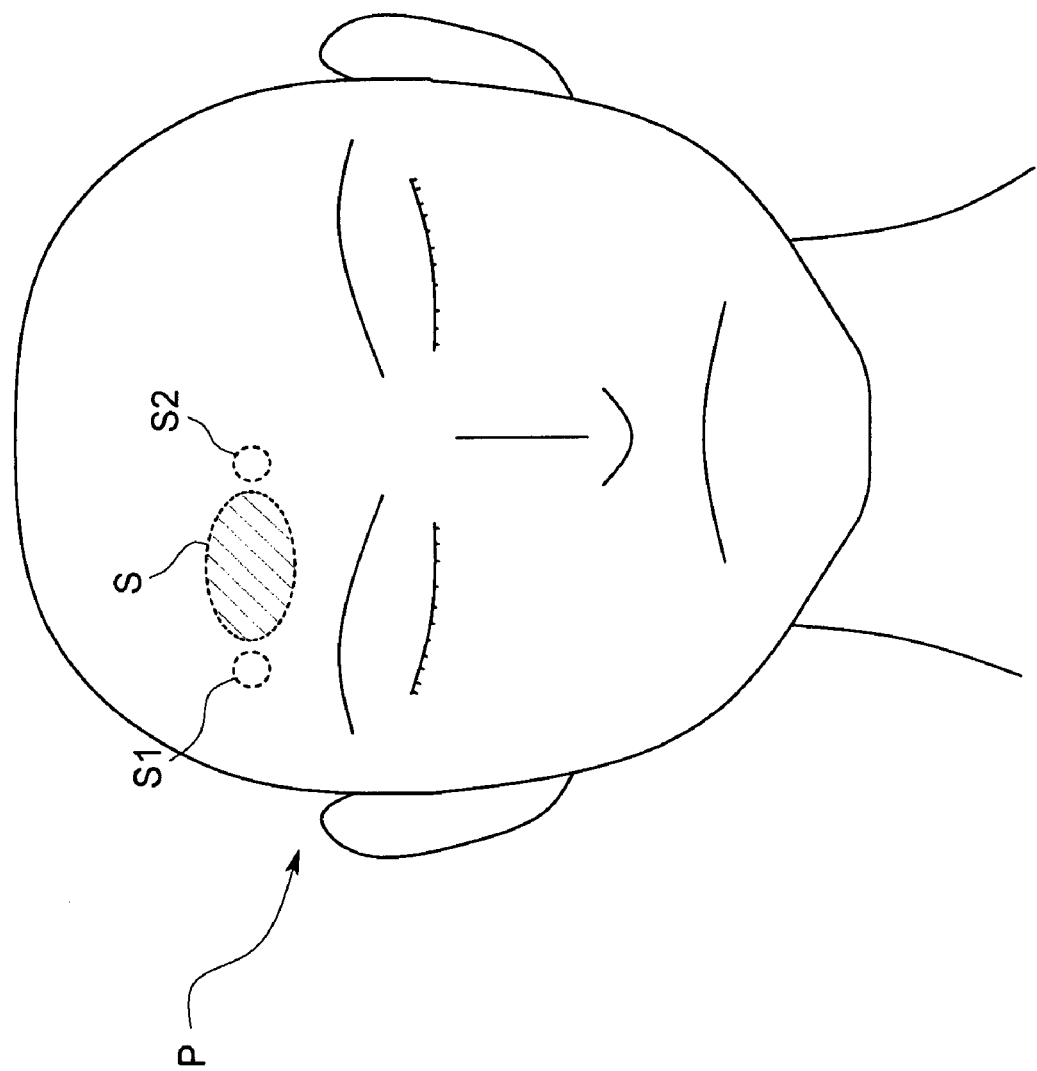
FIG. 2 is an explanatory view of a region showing a predetermined measuring region in accordance with the embodiment.

In this embodiment, the measuring portion 1 is a type of one channel, namely, having a pair of a light incident portion and a light receiving portion wherein each of the light incident portion and the light receiving portion is mounted on a predetermined area S1 and a predetermined area S2 respectively of a forehead of the subject P, as shown in FIG. 2, and measures the amount of oxyhemoglobin and the amount of deoxyhemoglobin in the predetermined measuring region S between the predetermined areas S1 and S2. The predetermined measuring region S is a higher brain function portion and set at, for example, the frontal lobe of the subject P in this embodiment. In order to determine the predetermined measuring region S, first a brain structural image of the subject P is obtained by the use of a device such as an MRI for measuring a brain structure and then the predetermined measuring region S is determined based on the above-obtained brain structural image. More concretely, the predetermined measuring region S locates in a region of a right prefrontal area where the brains protrude most. Substantial reasons for this are the right prefrontal area is a region other than a region dominating language, the right prefrontal area is considered to be related to a graphics processing according to an antecedent study and the right prefrontal area is easy to measure because the area has no hair.

The predetermined work is a work to draw lines, for example, to draw lines vertical to parallel lines of a 5 millimeter interval that have been described beforehand one after another at a distance as narrow as possible so as not to protrude from the parallel lines with a dominant hand. Five cycles are repeated with 10 seconds rest, 20 seconds drawing (the predetermined work) and 30 seconds rest as a cycle.

The diachronic change data producing portion 2 chronologically obtains the amount of oxyhemoglobin and the amount of deoxyhemoglobin measured by the measuring portion 1 over the above-mentioned five cycles with sampling at predetermined intervals and stores the amount in a predetermined memory portion so as to produce diachronic change data as data showing diachronic change of the amount of the oxyhemoglobin and the amount of the deoxyhemoglobin and a total hemoglobin amount calculated by the amounts of oxyhemoglobin and deoxyhemoglobin. In this embodiment the data are processed in a digital manner by the use of a CPU, however, it is a matter of course that the data may be processed in an analog manner so as to produce diachronic change data.

The waveform output portion 3 outputs waveforms of diachronic change data in each work to a display or a printer when the predetermined work is repeatedly conducted by the subject P several times.

Following is an example of results wherein the subject P actually conducts the predetermined work by the use of the device 4 to measure a degree of acquisition in accordance with the embodiment.

Figures 4, 5:
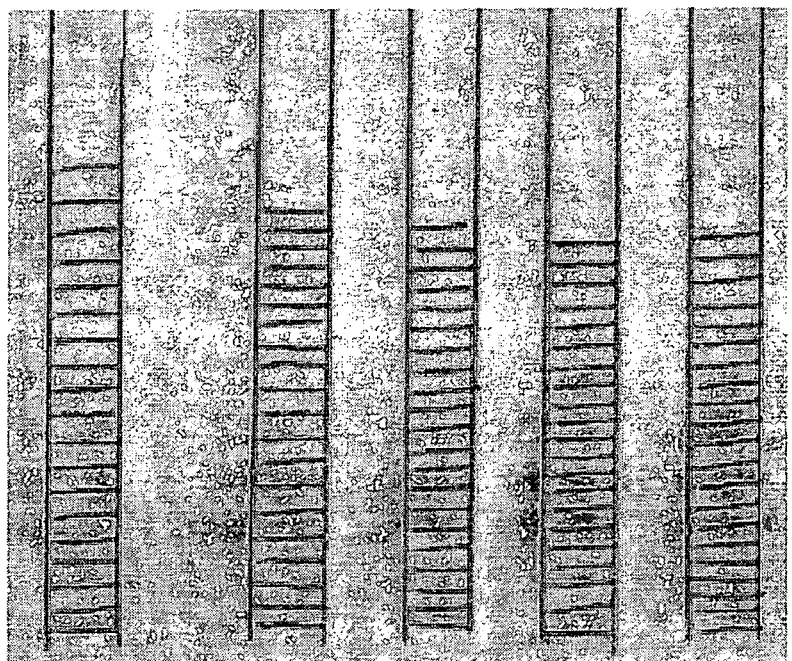
FIG. 4 is a drawing example showing a line drawn in each work in accordance with the embodiment.
FIG. 5 is an example of an achievement result of each work in accordance with the embodiment.

A result and an achievement of the work are shown in FIG. 4 and FIG. 5. According to FIG. 4 and FIG. 5, each distance between lines the subject P draws is wide and uneven during the work in the first and the second cycles and each distance between lines the subject P draws is narrow and a number of lines is increased on and after the work in the third cycle, which shows a tendency of stability on and after the work in the third cycle. As a result of this, it is conceivable that a degree of learning to the work for the subject P ascends on and after the work in the third cycle.

Figure 7:
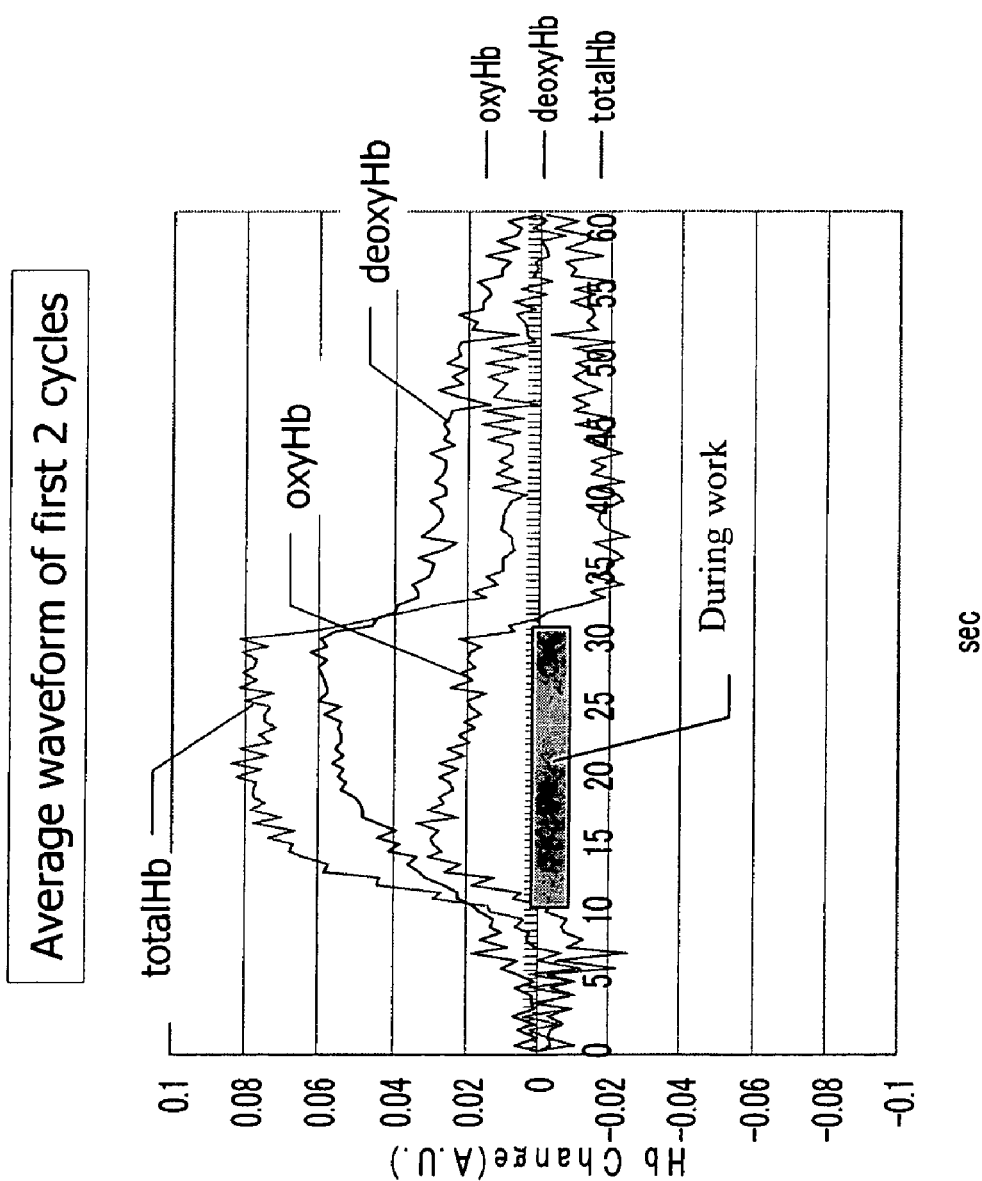
FIG. 7 is a waveform chart showing a waveform of diachronic change data in accordance with the embodiment.
Figure 8:
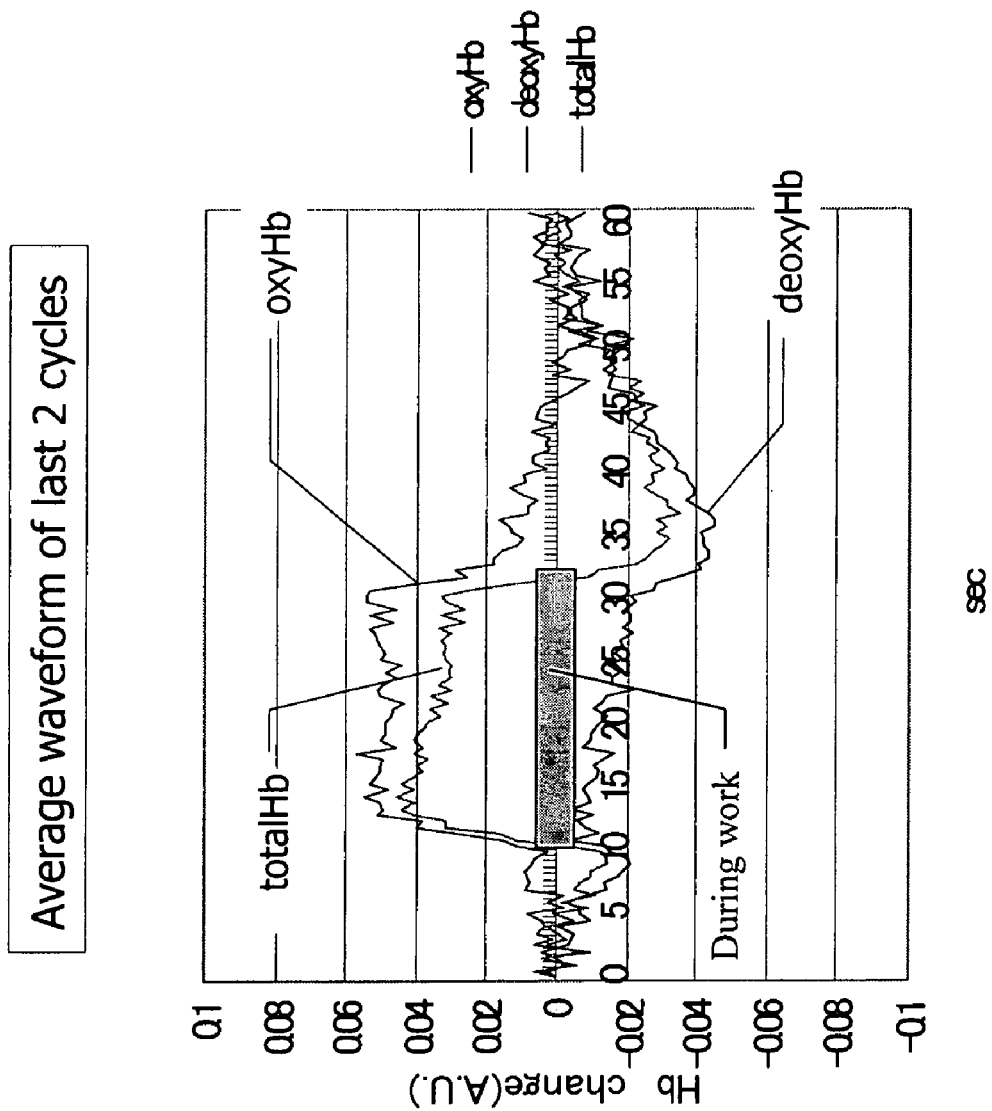
FIG. 8 is a waveform chart showing a waveform of diachronic change data in accordance with the embodiment.
Figure 9:
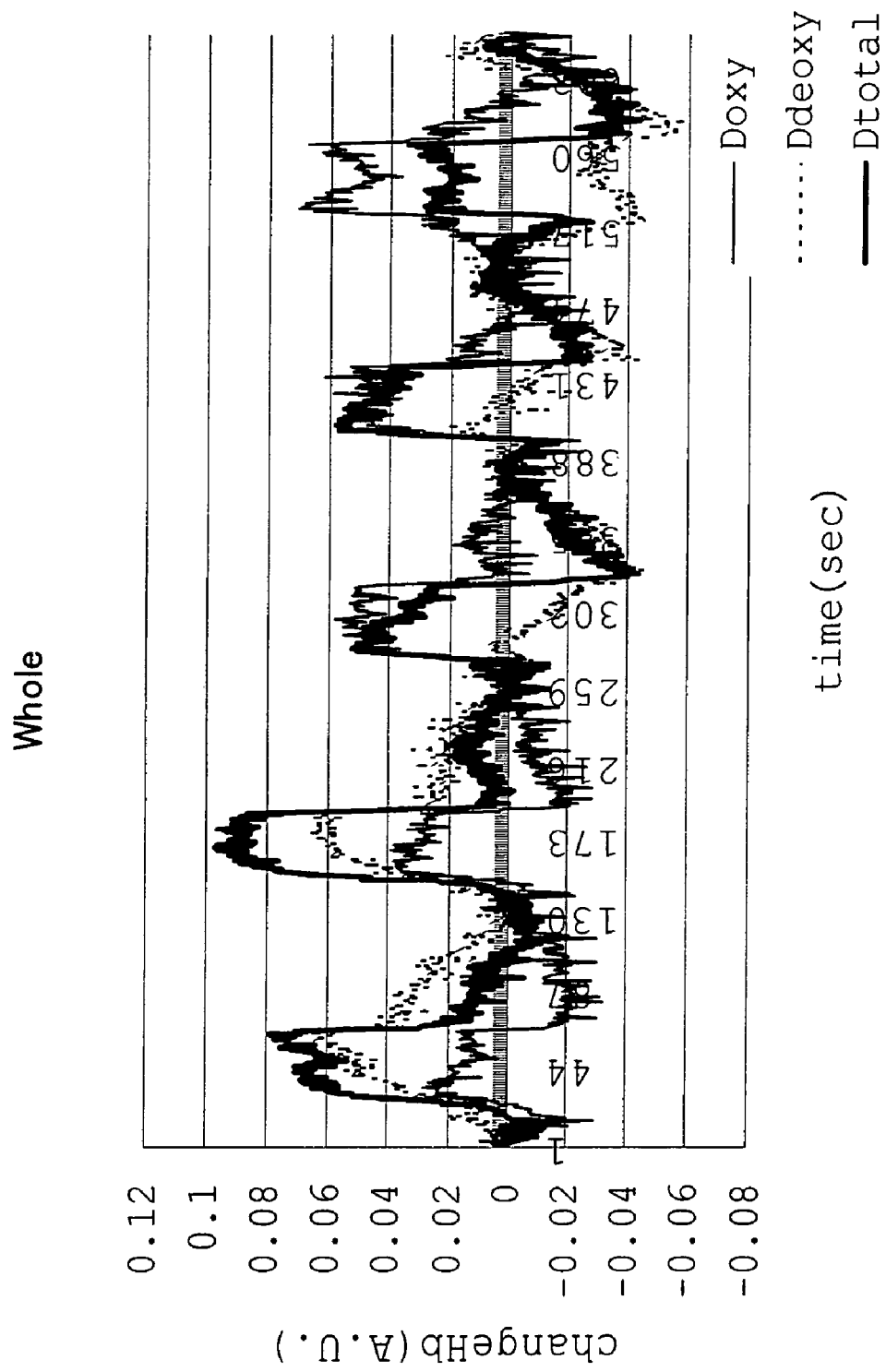
FIG. 9 is a waveform chart showing a waveform of diachronic change data in accordance with the embodiment.

FIG. 7, FIG. 8 and FIG. 9 show a waveform output result of the device 4 to measure a degree of acquisition and a graph wherein diachronic change data of a hemoglobin amount are output chronologically in a form of a waveform in each work.

Figure 6:
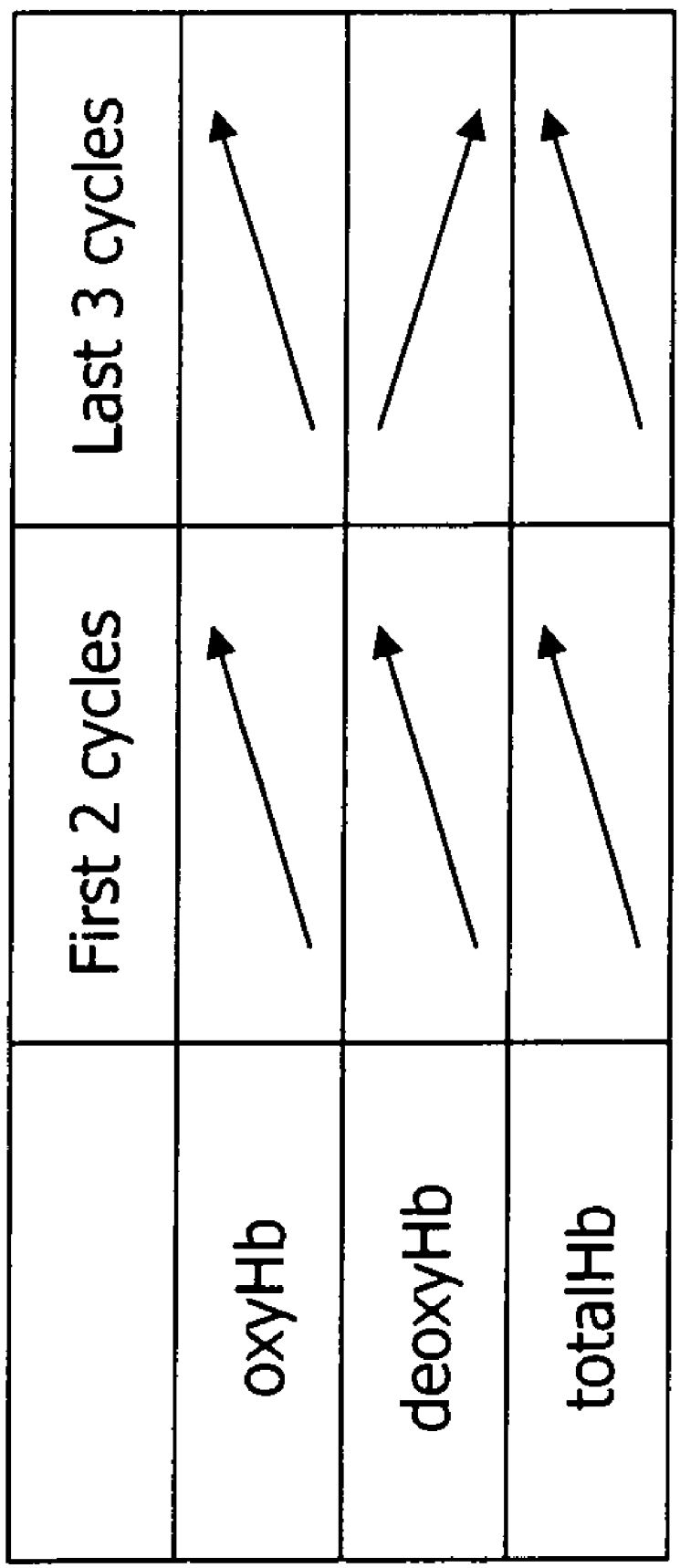
FIG. 6 is a tendency explanatory view showing a tendency of a waveform of diachronic change data in accordance with the embodiment.

A characteristic result revealed from those graphs is a change of the amount of deoxyhemoglobin. As a tendency of the waveform is shown in FIG. 6, if we focus attention on each cycle, both the amount of oxyhemoglobin and the amount of deoxyhemoglobin increase in conjunction with initiation of the work and both amounts decrease in conjunction with termination of the work during the work in the first two cycles. On the other hand, the amount of oxyhemoglobin increases and the amount of deoxyhemoglobin remains unchanged or decreases in conjunction with initiation of the work during the work in the last three cycles, which means that an outstanding inverted phenomenon occurs. The inverted phenomenon coincides with an improvement in a degree of acquisition to a work for the subject P.

Further, the amount of oxyhemoglobin is compared in each work. According to FIG. 9, the amount of oxyhemoglobin increases compared with a former cycle during the first three cycles and the amount of oxyhemoglobin hardly increases at all or decreases after the first three cycles, namely an increasing rate slowdowns after the first three cycles compared with the first three cycles. This tendency coincides with conventional study's findings that oxyhemoglobin is closely related with a brain function and supports a fact that the inverted phenomenon of the amount of deoxyhemoglobin shows the improvement in a degree of acquisition. By making use of this in order to further improve reliability of judging the degree of acquisition, the degree of acquisition can be judged to improve when both the inverted phenomenon of the amount of deoxyhemoglobin and the increasing rate lowering phenomenon are recognized.

Further, an absolute value of the total hemoglobin amount during the work in the last three cycles tends to decrease compared with the work in the first two cycles. A characteristic difference of waveforms is shown between the work in the first two cycles and the work in the last three cycles. The same tendency is obtained to other work such as writing Chinese characters.

As is clear from the above, a degree of acquisition to a work for a subject P can be obtained objectively from a characteristic difference of the waveform by comparison of waveforms of diachronic change data of the blood amount or/and the blood amount component by the use of the device 4 to measure a degree of acquisition. As a result of this, it is possible for an educator to obtain a degree of acquisition of a learner during education without imposing a special burden such as an examination to the learner and it is also possible to provide a development of a new educational method or an establishment of objective guidelines of an educational curriculum with a big potential.

In addition, since the device 4 makes use of the near-infrared spectroscopy, the device 4 is non-invasive and small in constraining degree for the subject P compared with other measuring device such as an fMRI. In addition the predetermined measuring region S is set at the frontal lobe that is easy to mount the device 4, which makes it possible to conduct the measurement under a natural environment.

Further, since the near-infrared spectroscopy is superior in time resolution, a degree of acquisition for a learner can be obtained on the spot in real time. An arrangement of the device 4 making use of the near-infrared spectroscopy is primarily simple. In addition to this, since the device 4 in accordance with the embodiment is simple in arrangement having one channel and does not require a complicated process such an image processing, the arrangement of the device 4 can be simplified in a cy-press manner.

The present claimed invention may variously be modified. For example, in case the subject P conducts different works, a degree of mastership (acquisition) and strong and weak points to each work for the subject P can be obtained by comparison of diachronic change data in each work.

In addition, a degree of acquisition to the work for the subject P can also be obtained with outputting diachronic change data to one work alone by making use of the result that the amount of deoxyhemoglobin does not increase in case the degree of acquisition to the work for the subject P is high.

Further, since the diachronic change of the amount of deoxyhemoglobin shows the above-mentioned distinctly remarkable difference (namely, whether the inverted phenomenon occurs or not) between a case that the degree of acquisition is high and a case that the degree of acquisition is low, by making use of this it is possible to provide an acquisition degree calculating portion that automatically calculates the degree of acquisition to each work for the subject P based on the diachronic change data with ease. For example, represented is that the degree of acquisition to each work for the subject P is determined high when the amount of deoxyhemoglobin remains generally unchanged or decreases irrespective of time change in diachronic change data during a work.

It is a matter of course that it is still more preferable to improve a reliability of automatically calculating the acquisition degree by further providing the diachronic change data of the amount of oxyhemoglobin or the diachronic change data of the amount of total hemoglobin as a parameter and providing a statistical work or the like. As a concrete example represented is that the degree of acquisition is determined high when the increasing rate lowering phenomenon of the amount of oxyhemoglobin between cycles is calculated.

If the acquisition degree calculating portion is arranged, the degree of acquisition can be determined more objectively and the waveform output portion 3 can be dispensable as well.

In case a posture when the subject P conducts a work is different from a posture when the subject P does not conduct the work, there might be an error in calculating a degree of acquisition because of an offset against the diachronic change data due to brain activities in connection with a change of the posture. In order to avoid this influence, it is preferable that the blood amount or/and the blood component amount is measured in a state the subject P does not conduct the work with taking a posture of conducting the work and a diachronic change of a value that is calculated by subtracting a blood amount or/and a blood component amount when the subject P conducts the work from the blood amount or/and the blood component amount measured in the state is assumed to be the diachronic change data.

It is a matter of course that a posture fixing device may be used to take a same posture when the subject P conducts a work and the subject P does not conduct the work.

The present claimed invention is not limited to the above-described embodiment and may be variously modified without departing from the spirit of the invention.

As mentioned above, in accordance with the present claimed invention, a degree of acquisition to a work for a subject P can be obtained objectively from the waveform of diachronic change data waveform of the blood volume amount or/and the blood component amount in a predetermined region of brains of the subject P. As a result of this, it is possible for an educator to obtain a degree of acquisition of a learner during education without imposing a special burden such as an examination to the learner and it is also possible to provide a development of a new educational method or an establishment of objective guidelines of an educational curriculum with a big potential. In addition, since the present claimed invention only detects diachronic change of the blood volume amount or/and the blood component amount and outputs waveforms, there is no need of a complicated processing nor mechanisms such as an image processing.

Further, since the device in accordance with the present claimed invention measures a blood volume amount or/and a blood component amount, it is possible to conduct a measurement under a non-invasive condition without constraining a movement of the subject with a simple arrangement, thereby to conduct a measurement under a natural environment, for example, by making use of a near-infrared spectroscopy. Further, since the near-infrared spectroscopy is superior in time resolution, a degree of acquisition for a learner can be obtained on the spot in real time.

What is claimed is:

1. A device to measure a degree of acquisition comprising:
    a measuring portion that measures a deoxy-Hb amount in a predetermined measuring region of a brain of a subject when the subject repeatedly conducts one work several times;
    a diachronic change data producing portion that obtains the deoxy-Hb amount measured in the above-mentioned measuring portion chronologically and produces diachronic change data as data showing diachronic change of a blood volume amount or/and a blood component amount;
    a waveform output portion that outputs a waveform of the diachronic change data in each work; and
    an acquisition degree determining portion that determines a degree of acquisition of the subject for each repetition of the work based on the diachronic change data, the acquisition degree determining portion determining that the acquisition degree is low when the deoxy-Hb amount increases on the initiation of the work and determining that the acquisition degree is high when the deoxy-Hb amount remains generally unchanged or decreases irrespective of time change in diachronic change data during performing the work.

2. The device to measure a degree of acquisition described in claim 1, wherein the predetermined measuring region is an area corresponding to a higher brain function portion.

3. The device to measure a degree of acquisition described in claim 1, wherein the predetermined measuring region is set at the frontal lobe.

4. The device to measure a degree of acquisition described in claim 1, wherein the measuring portion measures the deoxy-Hb amount by making use of a near-infrared spectroscopy.

5. The device to measure a degree of acquisition described in claim 4, wherein the measuring portion is a type of one channel.

6. The device to measure a degree of acquisition described in claim 1, in case a posture when the subject conducts the work is different from a posture when the subject does not conduct the work, wherein the deoxy-Hb amount is measured in a state when the subject does not conduct the work, but has the same posture as if the subject were conducting the work, and a diachronic change of a value calculated by subtracting a deoxy-Hb amount when the subject conducts the work from the deoxy-Hb amount measured in the above state is assumed to be the diachronic change data.

7. A device to measure a degree of acquisition of a work skill comprising:
    a measuring portion that measures one of a blood volume amount and a blood component amount in a predetermined measuring portion of a brain of a subject, during a first measurement when the subject is not working and during a second measurement when the subject is working from a start period to the completion point of time of the assignment of the work;
    a diachronic change data producing portion that obtains one of the blood volume amount and the blood component amount measured in the above-mentioned measuring portion chronologically and produces diachronic change data as data showing diachronic change of the blood volume amount or/and the blood component amount based on the first measurement and the second measurement; and
    an acquisition degree determining portion that calculates that a degree of acquisition of the work skill for the subject is high when the diachronic change data remains generally unchanged or decreases irrespective of time changes from the start period to the completion point of time of the working activity.

8. The device to measure a degree of acquisition described in claim 7, wherein that the predetermined measuring region is an area corresponding to a higher brain function portion.

9. The device to measure a degree of acquisition described in claim 7, wherein the predetermined measuring region is set at the frontal lobe.

10. A device for measuring strategy acquisition when a subject repetitively performs a predetermined assignment of work comprising:

a measuring portion that measures a deoxyhemoglobin amount in the blood in a predetermined measuring region of a brain of a subject during a first measurement when the subject is not working and during a second measurement from a start point to the completion point of time of the assignment of work for each performance of the work;

a diachronic change data producing portion that obtains the deoxyhemoglobin amount in the blood measured by the above-mentioned measuring portion chronologically and that produces diachronic change data showing change of the deoxyhemoglobin amount in the blood from the first measurement and the second measurement results; and an acquisition degree determining portion that calculates a degree of acquisition for each assignment of work performed by the subject by determining that a degree of acquisition of the work by the subject is high when the amount of deoxyhemoglobin tends to remain generally unchanged or decreases in the diachronic change data during the work in spite of the lapse of time and outputs the result.

\* \* \* \* \*